United States Patent
Qin et al.

(10) Patent No.: US 7,057,056 B1
(45) Date of Patent: Jun. 6, 2006

(54) EPOXIDATION CATALYST

(75) Inventors: Kun Qin, Chadds Ford, PA (US); Roger A. Grey, West Chester, PA (US); Peter J. Whitman, Glen Mills, PA (US)

(73) Assignee: Lyondell Chemical Technology, L.P., Greenville, DE (US)

( * ) Notice: Subject to any disclaimer, the term of this patent is extended or adjusted under 35 U.S.C. 154(b) by 12 days.

(21) Appl. No.: 11/016,053

(22) Filed: Dec. 17, 2004

(51) Int. Cl.
*C07D 301/19* (2006.01)
*C07D 301/12* (2006.01)

(52) U.S. Cl. ...................... 549/529; 549/531
(58) Field of Classification Search ............... 549/529, 549/531
See application file for complete search history.

(56) References Cited

U.S. PATENT DOCUMENTS

| | | | |
|---|---|---|---|
| 3,351,635 A | 11/1967 | Kollar | 260/348.5 |
| 4,367,342 A | 1/1983 | Wulff et al. | 549/529 |
| 4,410,501 A | 10/1983 | Taramasso et al. | 423/326 |
| 4,666,692 A | 5/1987 | Taramasso et al. | 423/326 |
| 4,833,260 A | 5/1989 | Neri et al. | 549/531 |
| 4,859,785 A | 8/1989 | Bellussi et al. | 549/531 |
| 4,937,216 A | 6/1990 | Clerici et al. | 502/62 |
| 5,859,265 A | 1/1999 | Muller et al. | 549/531 |
| 6,417,378 B1 | 7/2002 | Hancu | 549/533 |

FOREIGN PATENT DOCUMENTS

| | | |
|---|---|---|
| BE | 1001038 A7 | 6/1989 |
| JP | 4-352771 | 12/1992 |
| WO | WO 98/00413 | 1/1998 |

OTHER PUBLICATIONS

F. Di Renzo, et al., *Microporous Materials* 10 (1997) 283.
K. Edler et al., *J. Chem. Soc. Chem. Comm.* (1995) 155.

*Primary Examiner*—Amelia A. Owens
(74) *Attorney, Agent, or Firm*—Kevin M. Carroll

(57) ABSTRACT

Titanium or vanadium zeolites are pretreated by contacting with an amino polyacid compound, such as ethylenediaminetetraacetic acid or a salt thereof, prior to use in olefin epoxidation with hydrogen peroxide.

20 Claims, No Drawings understand# EPOXIDATION CATALYST

FIELD OF THE INVENTION

This invention relates to an epoxidation process to produce epoxides from olefins and hydrogen peroxide using a titanium or vanadium zeolite catalyst that has been pre-treated by contacting with an amino polyacid compound, such as ethylenediaminetetraacetic acid or a salt thereof.

BACKGROUND OF THE INVENTION

Many different methods for the preparation of epoxides have been developed. Generally, epoxides are formed by the reaction of an olefin with an oxidizing agent in the presence of a catalyst. The production of propylene oxide from propylene and an organic hydroperoxide oxidizing agent, such as ethylbenzene hydroperoxide or tert-butyl hydroperoxide, is commercially practiced technology. This process is performed in the presence of a solubilized molybdenum catalyst, see U.S. Pat. No. 3,351,635, or a heterogeneous titania on silica catalyst, see U.S. Pat. No. 4,367,342. Another commercially practiced technology is the direct epoxidation of ethylene to ethylene oxide by reaction with oxygen over a silver catalyst. Unfortunately, the silver catalyst has not proved useful in commercial epoxidation of higher olefins.

Besides oxygen and alkyl hydroperoxides, another oxidizing agent useful for the preparation of epoxides is hydrogen peroxide. U.S. Pat. Nos. 4,833,260, 4,859,785, and 4,937,216, for example, disclose the epoxidation of olefins with hydrogen peroxide in the presence of a titanium silicate catalyst.

Much current research is conducted in the direct epoxidation of olefins with oxygen and hydrogen. In this process, it is believed that oxygen and hydrogen react in situ to form an oxidizing agent. Many different catalysts have been proposed for use in the direct epoxidation of higher olefins. Typically, the catalyst comprises a noble metal that is supported on a titanosilicate. For example, JP 4-352771 discloses the formation of propylene oxide from propylene, oxygen, and hydrogen using a catalyst containing a Group VIII metal such as palladium on a crystalline titanosilicate. The Group VIII metal is believed to promote the reaction of oxygen and hydrogen to form a hydrogen peroxide in situ oxidizing agent. U.S. Pat. No. 5,859,265 discloses a catalyst in which a platinum metal, selected from Ru, Rh, Pd, Os, Ir and Pt, is supported on a titanium or vanadium silicalite. Other direct epoxidation catalyst examples include gold supported on titanosilicates, see for example PCT Intl. Appl. WO 98/00413.

One disadvantage of the described direct epoxidation catalysts is that they are prone to produce by-products such as glycols or glycol ethers formed by the ring-opening of the epoxide product or alkane by-product formed by the hydrogenation of olefin. U.S. Pat. No. 6,417,378 describes a direct olefin epoxidation process in which the selectivity for the reaction of olefin, oxygen, and hydrogen in the presence of a noble metal-containing titanium zeolite is enhanced by contacting the titanium zeolite with a leaching agent such as lactic acid.

As with any chemical process, it is desirable to attain still further improvements in the epoxidation methods and catalysts. We have discovered an effective, convenient process to form an epoxidation catalyst and its use in the epoxidation of olefins.

SUMMARY OF THE INVENTION

The invention is a process for producing epoxides from olefins and hydrogen peroxide using a pre-treated titanium or vanadium zeolite catalyst, wherein the zeolite catalyst is pre-treated by contacting with an amino polyacid compound. The process of the invention results in higher selectivity to the desired epoxide.

DETAILED DESCRIPTION OF THE INVENTION

The epoxidation process of the invention utilizes a titanium or vanadium zeolite. Titanium or vanadium zeolites comprise the class of zeolitic substances wherein titanium or vanadium atoms are substituted for a portion of the silicon atoms in the lattice framework of a molecular sieve. Such substances, and their production, are well known in the art. See for example, U.S. Pat. Nos. 4,410,501 and 4,666,692.

Suitable titanium or vanadium zeolites are those crystalline materials having a porous molecular sieve structure with titanium or vanadium atoms substituted in the framework. The choice of titanium or vanadium zeolite employed will depend upon a number of factors, including the size and shape of the olefin to be epoxidized. For example, it is preferred to use a relatively small pore titanium or vanadium zeolite such as a titanium silicalite if the olefin is a lower aliphatic olefin such as ethylene, propylene, or 1-butene. Where the olefin is propylene, the use of a TS-1 titanium silicalite is especially advantageous. For a bulky olefin such as cyclohexene, a larger pore titanium or vanadium zeolite such as a zeolite having a structure isomorphous with zeolite beta may be preferred.

Particularly preferred titanium or vanadium zeolites include the class of molecular sieves commonly referred to as titanium silicalites, particularly "TS-1" (having an MFI topology analogous to that of the ZSM-5 aluminosilicate zeolites), "TS-2" (having an MEL topology analogous to that of the ZSM-11 aluminosilicate zeolites), and "TS-3" (as described in Belgian Pat. No. 1,001,038). Titanium-containing molecular sieves having framework structures isomorphous to zeolite beta, mordenite, ZSM-48, ZSM-12, and MCM-41 are also suitable for use. The titanium zeolites preferably contain no elements other than titanium, silicon, and oxygen in the lattice framework, although minor amounts of boron, iron, aluminum, sodium, potassium, copper and the like may be present.

Preferred titanium zeolites will generally have a composition corresponding to the following empirical formula $xTiO_2$ $(1-x)SiO_2$ where x is between 0.0001 and 0.5000. More preferably, the value of x is from 0.01 to 0.125. The molar ratio of Si:Ti in the lattice framework of the zeolite is advantageously from 9.5:1 to 99:1 (most preferably from 9.5:1 to 60:1). The use of relatively titanium-rich zeolites may also be desirable.

The synthesis of titanium or vanadium zeolites is well known in the art. Titanium or vanadium zeolite synthesis typically comprises reacting a titanium or vanadium compound, a silicon source, and a templating agent at a temperature and for a time sufficient to form a titanium or vanadium zeolite. After the reaction mixture is formed, it is reacted at a temperature and a time sufficient to form a molecular sieve. Typically, the reaction mixture is heated at a temperature of about 100° C. to about 250° C. for a period of about 0.5 hours to about 96 hours in a sealed vessel under autogenous pressure. Preferably, the reaction mixture is heated at a temperature range from about 125° C. to about 200° C., most preferably from about 150° C. to about 180° C. After the desired reaction time, the titanium or vanadium zeolite is recovered. Suitable zeolite recovery methods include filtration and washing (typically with deionized water), rotary evaporation, centrifugation, and the like. The titanium or vanadium zeolite may be dried at a temperature greater than about 20° C., preferably from about 50° C. to about 200° C. Preferably, the titanium or vanadium zeolite is heated at temperatures greater than about 400° C., typically from about 450° C. to about 1000° C., and preferably from about 475° C. to about 600° C., in order to decompose the templating agent contained in the pores. However, for the process of the invention it is not necessary for the titanium or vanadium zeolite to be heated prior to pre-treatment with the amino polyacid compound. If the as-synthesized titanium or vanadium zeolite is produced in the form of a powder, it may be spray dried, pelletized or extruded prior to pre-treatment with the amino polyacid compound. If spray dried, pelletized or extruded, the titanium or vanadium zeolite may additionally comprise a binder or the like and may be molded, spray dried, shaped or extruded into any desired form prior to or after the pre-treatment with amino polyacid compound.

The process of the invention utilizes a pre-treated titanium or vanadium zeolite. The pre-treated titanium or vanadium zeolite is formed by contacting a titanium or vanadium zeolite with an amino polyacid compound. An amino polyacid is any compound that contains at least one amine functionality and two or more acid functionalities such as a carboxylic, phosphonic, or sulfonic acids; three or more acid functionalities are preferred; and four or more acid functionalities are most preferred. Amino polyacids include amino polycarboxylic acids, amino polyphosphonic acids, and amino polysulfonic acids. Amino polyacids also include the related salts of the amino polyacids, for instance the alkali, alkaline earth metal, or ammonium salts of the amino polyacids.

Preferred amino polycarboxylic acids include alkylenediamine polyacetic acids, nitrilotriacetic acid, and iminodiacetic acid. Preferred alkylene diamine polyacetic acids include ethylenediaminetetraacetic acid, ethylenediaminetriacetic acid, and the like, and their salts thereof. Preferred amino polyphosphonic acids include aminodiphosphonic acids such as (dimethylamino)methylenediphosphonic acid and (aminoethylene)diphosphonic acid, and their salts. Preferred amino polysulfonic acids include amino disulfonic acids such as 2-methylaminobutane-1,4-disulfonate, 1-amino-8-naphthol-3,6-disulfonic acid, 4,4'-diamino-1,1'-bianthraquinonyl-3,3'-disulfonic acids, and the like, and their salts. Particularly preferred amino polyacids are the amino polycarboxylic acids, and especially preferred include the alkylenediamine polyacetic acids, and the salts thereof. Mixtures of amino polyacids may also be contacted with the titanium or vanadium zeolite.

The titanium or vanadium zeolite is contacted with a solution of an amino polyacid compound. The solution is typically an aqueous solution, but may be any other solvent that dissolves the amino polyacid compound. Any conventional contacting procedure is suitable. The contacting temperature is not crucial to the invention, however lower temperatures may require a longer contact period. Preferably, the titanium or vanadium zeolite is contacted with the amino polyacid compound at a temperature greater than 20° C. More preferred wash temperatures are greater than 40° C., most preferably from 40° C. to 80° C. Pressures of from 0 to 1000 psig are generally useful for purposes of this invention. Preferably, the pressure is sufficient to maintain the solution substantially as a liquid phase when elevated temperatures are used.

The contacting procedure may be carried out in a continuous or a batch-type process. In a fixed bed embodiment of the invention, it is preferred to pass the contacting amino polyacid compound solution through the titanium or vanadium zeolite as a flowing stream such that solution effluent is continually carried away from the fixed bed. The contacting solution may preferentially be recirculated. Liquid hourly space velocities in the range of from 0.1 to 24 are generally satisfactory. When the contacting is performed as a batch-type process, the titanium or vanadium zeolite may be contacted with amino polyacid compound solution by agitating the solution and removing the supernatant solution. The contacting time is preferably in the range of from about 1 hour to 30 days.

Contacting preferentially also encompasses separating the amino polyacid compound solution from the contacted zeolite. For instance, after contacting, the titanium or vanadium zeolite may be collected by filtration, centrifugation, decantation, or other such mechanical means prior to use in the epoxidation reaction of the invention. After contacting and collecting the zeolite by filtration, centrifugation, decantation, or other such mechanical means, the titanium or vanadium zeolite may also be dried. The drying may be performed under vacuum, with heating, or a combination. Preferably, the titanium or vanadium zeolite is heated at a temperature greater than 350° C. in the presence of an oxygen-containing atmosphere or an inert gas to calcine or pyrolyze the zeolite after the contacting step. Alternatively, the titanium or vanadium zeolite may be pyrolyzed by heating at a temperature greater than 350° C. in the presence an inert gas following the contacting step. The contacted titanium or vanadium zeolite may also be washed by any suitable washing procedure. Preferable wash solvents include water, alcohols, ketones, and the like.

After contacting the zeolite with the amino polyacid compound, the titanium or vanadium zeolite may be used in the epoxidation process as a powder or as a large particle size solid. If the pre-treated titanium or vanadium zeolite is still in the form of a powder, it may preferably be spray dried, pelletized or extruded prior to epoxidation. If spray dried, pelletized or extruded, the titanium or vanadium zeolite may additionally comprise a binder or the like and may be molded, spray dried, shaped or extruded into any desired form.

The epoxidation process of the invention comprises contacting an olefin and hydrogen peroxide in the presence of the pre-treated titanium or vanadium zeolite catalyst. Suitable olefins include any olefin having at least one carbon—carbon double bond, and generally from 2 to 60 carbon atoms. Preferably the olefin is an acyclic alkene of from 2 to 30 carbon atoms; the process of the invention is particularly suitable for epoxidizing $C_2$–$C_6$ olefins. More than one double bond may be present, as in a diene or triene for example. The olefin may be a hydrocarbon (i.e., contain only carbon and hydrogen atoms) or may contain functional groups such as halide, carboxyl, hydroxyl, ether, carbonyl, cyano, or nitro groups, or the like. The process of the invention is especially useful for converting propylene to propylene oxide.

The hydrogen peroxide may be generated prior to use in the epoxidation reaction. Hydrogen peroxide may be derived from any suitable source, including oxidation of secondary alcohols such as isopropanol, the anthraquinone process, and from direct reaction of hydrogen and oxygen. The concentration of the aqueous hydrogen peroxide reactant added into the epoxidation reaction is not critical. Typical hydrogen peroxide concentrations range from 0.1 to 90 weight percent hydrogen peroxide in water, preferably 1 to 5 weight percent.

The amount of hydrogen peroxide to the amount of olefin is not critical, but most suitably the molar ratio of hydrogen peroxide:olefin is from 100:1 to 1:100, and more preferably in the range of 10:1 to 1:10. One equivalent of hydrogen peroxide is theoretically required to oxidize one equivalent of a mono-unsaturated olefin substrate, but it may be desirable to employ an excess of one reactant to optimize selectivity to the epoxide.

The hydrogen peroxide may also be generated in situ by the reaction of hydrogen and oxygen in the presence of a noble metal catalyst. Although any sources of oxygen and hydrogen are suitable, molecular oxygen and molecular hydrogen are preferred.

While any noble metal catalyst can be utilized (i.e., gold, silver, platinum, palladium, iridium, ruthenium, osmium metal catalysts), either alone or in combination, palladium, platinum and gold metal catalysts are particularly desirable. Suitable noble metal catalysts include high surface area noble metals, noble metal alloys, and supported noble metal catalysts. Examples of suitable noble metal catalysts include high surface area palladium, colloidal palladium, and palladium alloys. However, particularly preferred noble metal catalysts are supported noble metal catalysts comprising a noble metal and a support.

For supported noble metal catalysts, the support is preferably a porous material. Supports are well-known in the art. There are no particular restrictions on the type of support that are used. For instance, the support can be inorganic oxides, inorganic chlorides, carbon, and organic polymer resins. Preferred inorganic oxides include oxides of Group 2, 3, 4, 5, 6, 13, or 14 elements. Particularly preferred inorganic oxide supports include silica, alumina, titania, zirconia, ceria, niobium oxides, tantalum oxides, molybdenum oxides, tungsten oxides, amorphous titania-silica, amorphous zirconia-silica, amorphous niobia-silica, ceria-silica, and the like. Preferred organic polymer resins include polystyrene, styrene-divinylbenzene copolymers, crosslinked polyethyleneimines, and polybenzimidazole. Suitable supports also include organic polymer resins grafted onto inorganic oxide supports, such as polyethylenimine-silica. Preferred supports also include carbon. Particularly preferred supports include silica, silica-aluminas, titania, zirconia, ceria, niobia, and carbon.

Preferably, the support has a surface area in the range of about 10 to about 700 $m^2/g$, more preferably from about 50 to about 500 $m^2/g$, and most preferably from about 100 to about 400 $m^2/g$. Preferably, the pore volume of the support is in the range of about 0.1 to about 4.0 mL/g, more preferably from about 0.5 to about 3.5 mL/g, and most preferably from about 0.8 to about 3.0 mL/g. Preferably, the average particle size of the support is in the range of about 0.1 to about 500 μm, more preferably from about 1 to about 200 μm, and most preferably from about 10 to about 100 μm. The average pore diameter is typically in the range of about 10 to about 1000 Å, preferably about 20 to about 500 Å, and most preferably about 50 to about 350 Å. In one preferred embodiment of the invention, the supported noble metal catalyst comprises a noble metal supported on the pre-treated titanium or vanadium zeolite. The supported noble metal catalyst may also comprise a mixture of noble metal-containing titanium or vanadium zeolite and noble metal-free titanium or vanadium zeolite. The noble metal-free titanium or vanadium zeolite is a titanium or vanadium-containing molecular sieve that is free of added noble is metal.

The supported noble metal catalyst contains a noble metal. While any of the noble metals can be utilized (i.e., gold, silver, platinum, palladium, iridium, ruthenium, osmium), either alone or in combination, palladium, platinum and gold are particularly desirable, and palladium is especially preferred. Typically, the amount of noble metal present in the supported catalyst will be in the range of from 0.001 to 20 weight percent, preferably 0.005 to 10 weight percent, and particularly 0.01 to 5 weight percent. The manner in which the noble metal is incorporated into the catalyst is not considered to be particularly critical. For example, the noble metal may be supported on the zeolite by impregnation, adsorption, precipitation, or the like. Alternatively, the noble metal can be incorporated into the zeolite by ion-exchange with, for example, tetraammine palladium dichloride or tetraammine palladium dinitrate.

There are no particular restrictions regarding the choice of noble metal compound or complex used as the source of the noble metal in the supported catalyst. For example, suitable compounds include the nitrates, sulfates, halides (e.g., chlorides, bromides), carboxylates (e.g. acetate, trifluoroacetate), and amine complexes of noble metals. The noble metal may be in an oxidation state anywhere from 0 to +4 or any combination of such oxidation states. To achieve the desired oxidation state or combination of oxidation states, the noble metal compound may be pyrolyzed, calcined, reduced, or a combination thereof. Satisfactory catalytic performance can, however, be attained without any pre-reduction. To achieve the active state of noble metal, the supported noble metal catalyst may undergo pretreatment such as thermal treatment in oxygen, nitrogen, vacuum, hydrogen, or air.

In one preferred embodiment of the invention, the epoxidation of olefin with hydrogen and oxygen is carried out in the presence of a noble metal-containing titanium or vanadium zeolite which comprises a noble metal and the pre-treated titanium or vanadium zeolite. In this particular embodiment, the titanium or vanadium zeolite may be pre-treated with amino polyacid either prior to or following incorporation of the noble metal. Preferably, the titanium or vanadium zeolite has been pre-treated with amino polyacid prior to noble metal incorporation. If the titanium or vanadium zeolite is pre-treated with amino polyacid prior to noble metal incorporation, the pre-treated titanium or vanadium zeolite should be heated at a temperature greater than 350° C. in order to remove the amino polyacid prior to introduction of noble metal. If heated, the pre-treated titanium or vanadium zeolite is heated at temperatures greater than 350° C., and more preferably from about 375° C. to about 800° C. The high temperature heating may be conducted in inert atmosphere which is substantially free of oxygen, such as nitrogen, argon, neon, helium or the like or mixture thereof. By "substantially free of oxygen", it is meant that the inert atmosphere contains less than 10,000 ppm mole oxygen, preferably less than 2000 ppm. Also, the heating may be conducted in an oxygen-containing atmosphere, such as air or a mixture of oxygen and an inert gas. Alternatively, the catalyst may also be heated in the presence of an inert gas such as nitrogen prior to heating in an oxygen-containing atmosphere. The heating process may be conducted such that the gas stream (inert, oxygen-containing, or both) is passed over the pre-treated titanium or vanadium zeolite. Alternatively, the heating may be performed in a static manner. The zeolite could also be agitated or stirred while being contacted with the gas stream.

The noble metal-containing titanium or vanadium zeolite catalyst may also comprise a mixture of palladium-containing titanium or vanadium zeolite and palladium-free titanium or vanadium zeolite. The palladium-free titanium or vanadium zeolite is a titanium or vanadium zeolite that is free of added palladium. The addition of a palladium-free titanium or vanadium zeolite has proven beneficial to productivity of the palladium that is present in the catalyst. Preferably, the palladium-free titanium or vanadium zeolite is also pre-treated with amino polyacid.

Depending on the olefin to be reacted, the epoxidation according to the invention can be carried out in the liquid phase, the gas phase, or in the supercritical phase. When a liquid reaction medium is used, the catalyst is preferably in the form of a suspension or fixed-bed. The process may be performed using a continuous flow, semi-batch or batch mode of operation.

If epoxidation is carried out in the liquid (or supercritical) phase, it is advantageous to work at a pressure of 1–100 bars and in the presence of one or more solvents. Suitable solvents include, but are not limited to, alcohols, water, supercritical $CO_2$, or mixtures thereof. Suitable alcohols include $C_1$–$C_4$ alcohols such as methanol, ethanol, isopropanol, and tert-butanol, or mixtures thereof. Fluorinated alcohols can be used. It is preferable to use mixtures of the cited alcohols with water.

If epoxidation is carried out in the liquid (or supercritical) phase, it is advantageous to use a buffer. The buffer will typically be added to the solvent to form a buffer solution. The buffer solution is employed in the reaction to inhibit the formation of glycols or glycol ethers during epoxidation. Buffers are well known in the art.

Buffers useful in this invention include any suitable salts of oxyacids, the nature and proportions of which in the mixture, are such that the pH of their solutions may range from 3 to 10, preferably from 4 to 9 and more preferably from 5 to 8. Suitable salts of oxyacids contain an anion and cation. The anion portion of the salt may include anions such as phosphate, carbonate, bicarbonate, carboxylates (e.g., acetate, phthalate, and the like), citrate, borate, hydroxide, silicate, aluminosilicate, or the like. The cation portion of the salt may include cations such as ammonium, alkylammoniums (e.g., tetraalkylammoniums, pyridiniums, and the like), alkali metals, alkaline earth metals, or the like. Examples include $NH_4$, $NBu_4$, $NMe_4$, Li, Na, K, Cs, Mg, and Ca cations. More preferred buffers include alkali metal phosphate and ammonium phosphate buffers. Buffers may preferably contain a combination of more than one suitable salt. Typically, the concentration of buffer in the solvent is from about 0.0001 M to about 1 M, preferably from about 0.001 M to about 0.3 M. The buffer useful in this invention may also include the addition of ammonia gas to the reaction system. The process of the invention may be carried out in a batch, continuous, or semi-continuous manner using any appropriate type of reaction vessel or apparatus such as a fixed-bed, transport bed, fluidized bed, stirred slurry, or CSTR reactor. The catalyst is preferably in the form of a suspension or fixed-bed. Known methods for conducting metal-catalyzed epoxidations of olefins using an oxidizing agent will generally also be suitable for use in this process. Thus, the reactants may be combined all at once or sequentially.

Epoxidation according to the invention is carried out at a temperature effective to achieve the desired olefin epoxidation, preferably at temperatures in the range of 0–150° C., more preferably, 20–120° C. Reaction or residence times of from about 1 minute to 48 hours, more preferably 1 minute to 8 hours will typically be appropriate. It is advantageous to work at a pressure of 1 to 100 atmospheres.

The following examples merely illustrate the invention. Those skilled in the art will recognize many variations that are within the spirit of the invention and scope of the claims.

EXAMPLE 1

EDTA Treatment of TS-1 Catalyst

TS-1 can be made according to any known literature procedure. See, for example, U.S. Pat. No. 4,410,501, DiRenzo, et. al., *Microporous Materials* (1997), Vol. 10, 283, or Edler, et. al., *J. Chem. Soc., Chem. Comm.* (1995), 155.

Catalyst 1A: Spray dried TS-1 (15 g, 80% TS-1, silica binder, 2.0 wt. % Ti, calcined at 550° C. in air) is suspended in a saturated aqueous ethylenediaminetetraacetic acid (EDTA) solution (150 mL of 0.5 wt. % EDTA) solution and stirred at 60° C. for 18 hours. After filtration and washing (3 times with 100 mL water), the obtained solid is air-dried at 110° C., and calcined in air at 550° C. for 4 hours. Catalyst 1A contains 1.8 wt. % Ti.

Catalyst 1B: Spray dried TS-1 (20 g, 80% TS-1, silica binder, 2.0 wt. % Ti, calcined at 550° C. in air) is suspended in an aqueous dipotassium ethylenediaminetetraacetic acid dihydrate ($K_2$EDTA) solution (300 g of 3 wt. % $K_2$EDTA solution) and stirred at 60° C. for 18 hours. After filtration, the collected solid is washed with water (3 times with 100 mL). The washed solid is then refluxed in an acetic acid solution (100 mL of 0.1M acetic acid) for 1 hour. After filtration and washing (3 times with 100 mL water), the obtained solid is air-dried at 110° C., and calcined in air at 550° C. for 4 hours. Catalyst 1B contains 1.8 wt. % Ti.

EXAMPLE 2

Epoxidation of Propylene with Hydrogen Peroxide

Spray dried TS-1 (as a comparative example), Catalysts 1A and 1B are used in batch epoxidation of propylene with hydrogen peroxide according to the following procedure:

A solution of methanol, water and hydrogen peroxide (40 g of solution, 84% MeOH, 11% $H_2O$, and 5% $H_2O_2$) is added to a 125-mL PARR reactor equipped with a stirring bar. The catalyst (0.15 g) is suspended in the reaction solution, and the reactor is charged with propylene (20 g). The closed system is then heated at 50° C. for 30 minutes. The concentration of unreacted hydrogen peroxide is determined by titration (sodium thiosulfate method) and the products are analyzed with GC.

The results are shown in Table 1.

EXAMPLE 3

Preparation of Pd/TS-1 Catalysts

Comparative Catalyst 3A: Spray dried TS-1 (16 g, 80% TS-1, silica binder, 2.0 wt. % Ti, calcined at 550° C. in air) is slurried in water (14 g). An aqueous solution of tetra ammine palladium dinitrate (0.299 g aqueous solution containing 5.37 wt. % Pd) is then added, and the slurry is stirred at 30° C. for 10 minutes. The pH is adjusted to 7.0 with 30 wt. % ammonium hydroxide and the slurry is stirred at 30° C. for an additional 35 minutes before adjusting the pH to 7.6. The slurry is filtered and the filter cake is washed with water (100 mL, three times). The solids are vacuum dried at 55° C. for 6 hours, then calcined in air at 300° C. for 4 hours. The calcined solids are then transferred to a quartz tube, heated to 100° C. and treated with 5 vol. % hydrogen in nitrogen (100 cc/min) for 1 hour. The dried solid contains 0.1 wt. % Pd and 2.0 wt. % Ti.

Catalyst 3B: Catalyst 3B is made according to the procedure of Comparative Catalyst 3A, except that Catalyst 1A (16 g) is used in place of the spray dried TS-1. The dried solid contains 0.1 wt. % Pd and 1.8 wt. % Ti.

Catalyst 3C: Catalyst 3C is made according to the procedure of Comparative Catalyst 3A, except that Catalyst 1B (16 g) is used in place of the spray dried TS-1. The dried solid contains 0.1 wt. % Pd and 1.8 wt. % Ti.

EXAMPLE 4

Direct Epoxidation of Propylene with Hydrogen and Oxygen

To evaluate the performance of the catalysts prepared in Example 3, the epoxidation of propylene using oxygen and hydrogen is carried out. The following procedure is employed.

A 0.1 M ammonium phosphate buffer solution is prepared by dissolving ammonium dihydrogen phosphate (($NH_4$)$H_2PO_4$, 11.5 g) in deionized water (900 g). Aqueous ammonium hydroxide (30% $NH_4OH$) is added to the solution until the pH reads 6 via a pH meter. The volume of the solution is then increased to exactly 1000 mL with deionized water.

A working solution is then prepared by diluting 125 g of the 0.1 M ammonium phosphate buffer solution with a further 125 g of deionized water, and mixing with methanol (750 g).

The reaction system consists a 300-cc stainless steel CSTR type reactor. Gas and liquid feeds enter the reactor, and exit through an outlet filter. Catalyst (6 g) and working solution (100 mL) are added to the reactor as a slurry. The slurry in the reactor is heated to 60° C. under about 300 psig, and is stirred at 1000 rpm. Additional working solution is pumped through the reactor at a rate of about 30 g/hr. The gas flow rates were about 4500 sccm (standard cubic centimeters per minute) of 5 vol. % oxygen in nitrogen, 280 sccm propylene, and 135 sccm hydrogen. Propylene oxide and equivalents ("POE"), which include propylene oxide ("PO"), propylene glycol, and glycol ethers, are produced during the reaction. The products coming out of the reactor (in both vapor and liquid phase) are analyzed by GC. The results of the GC analyses are used to calculate the selectivities shown in Table 2.

TABLE 1

BATCH EPOXIDATION RESULTS WITH HYDROGEN PEROXIDE USING TREATED AND UNTREATED CATALYSTS

| Catalyst | $H_2O_2$ Conversion (%) | PO produced (mmol) | POE produced (mmol) | Ti Productivity (mol POE/mol Ti/min) | PO/POE Selectivity (%)[1] |
|---|---|---|---|---|---|
| TS-1* | 68.2 | 0.233 | 0.251 | 20.1 | 92.8 |
| 1A | 65.6 | 0.232 | 0.245 | 21.8 | 94.5 |
| 1B | 51.0 | 0.186 | 0.194 | 17.2 | 96.0 |

*Comparative Example
[1]PO/POE Selectivity = moles PO/(moles PO + moles glycols + moles glycol ethers) * 100.

TABLE 2

CONTINUOUS DIRECT EPOXIDATION RESULTS

| Catalyst | Wt. % Pd | Productivity[1] | PO/POE Selectivity (%)[2] |
|---|---|---|---|
| 3A* | 0.1 | 0.48 | 85 |
| 3B | 0.1 | 0.55 | 89 |
| 3C | 0.1 | 0.45 | 90 |

*Comparative Example
[1]Productivity = grams POE produced/gram of catalyst per hour.
[2]PO/POE Selectivity = moles PO/(moles PO + moles glycols + moles glycol ethers) * 100.

We claim:

1. An epoxidation process which comprises reacting an olefin with hydrogen peroxide in the presence of a titanium or vanadium zeolite, wherein the zeolite is pre-treated by contacting with an amino polyacid compound.

2. The process of claim 1 wherein the zeolite is a titanium silicalite.

3. The process of claim 1 wherein the zeolite is TS-1.

4. The process of claim 1 wherein the olefin is a $C_2$–$C_6$ olefin.

5. The process of claim 1 wherein the amino polyacid compound is selected from the group consisting of amino polycarboxylic acids, amino polyphosphonic acids, amino polysulfonic acids, and mixtures thereof.

6. The process of claim 1 wherein the amino polyacid is selected from the group consisting of ethylenediaminetetraacetic acid, ethylenediaminetriacetic acid, nitrilotriacetic acid, iminodiacetic acid, and mixtures thereof.

7. The process of claim 1 wherein reaction of olefin and hydrogen peroxide is performed in a solvent selected from the group consisting of water, $C_1$–$C_4$ alcohols, supercritical $CO_2$, and mixtures thereof.

8. The process of claim 1 wherein the hydrogen peroxide is formed by the in situ reaction of hydrogen and oxygen in the presence of a noble metal catalyst.

9. The process of claim 8 wherein the noble metal catalyst comprises a noble metal and a support.

10. The process of claim 9 wherein the noble metal is selected from the group consisting of palladium, platinum, and gold.

11. The process of claim 9 wherein the support is selected from the group consisting of carbon, titania, zirconia, ceria, niobium oxides, silica, alumina, silica-alumina, tantalum oxides, molybdenum oxides, tungsten oxides, titania-silica, zirconia-silica, ceria-silica, niobia-silica, polystyrene, styrene-divinylbenzene copolymers, crosslinked polyethyleneimines, polybenzimidazole, and mixtures thereof.

12. An epoxidation process which comprises reacting an olefin, hydrogen and oxygen in the presence of a noble metal-containing titanium or vanadium zeolite catalyst comprising a noble metal and a titanium or vanadium zeolite, wherein the zeolite is pre-treated by contacting with an amino polyacid compound.

13. The process of claim 12 wherein the olefin is a $C_2$–$C_6$ olefin.

14. The process of claim 12 wherein the amino polyacid compound is selected from the group consisting of amino polycarboxylic acids, amino polyphosphonic acids, amino polysulfonic acids, and mixtures thereof.

15. The process of claim 12 wherein the amino polyacid is selected from the group consisting of ethylenediaminetetraacetic acid, ethylenediaminetriacetic acid, nitrilotriacetic acid, iminodiacetic acid, and mixtures thereof.

16. The process of claim 12 wherein reaction of olefin, hydrogen and oxygen is performed in a solvent selected from the group consisting of water, $C_1$–$C_4$ alcohols, supercritical $CO_2$, and mixtures thereof.

17. A process comprising contacting a titanium or vanadium zeolite with an amino polyacid compound selected from the group consisting of amino polycarboxylic acids, amino polyphosphonic acids, amino polysulfonic acids, and mixtures thereof.

18. The process of claim 17 further comprising heating the contacted titanium or vanadium zeolite at a temperature greater than 350° C.

19. The process of claim 17 further comprising washing the contacted titanium or vanadium zeolite.

20. The process of claim 17 wherein the amino polyacid is selected from the group consisting of ethylenediaminetetraacetic acid, ethylenediaminetriacetic acid, nitrilotriacetic acid, iminodiacetic acid, and mixtures thereof.

* * * * *